US006283896B1

(12) United States Patent
Grunfeld et al.

(10) Patent No.: US 6,283,896 B1
(45) Date of Patent: Sep. 4, 2001

(54) COMPUTER INTERFACE WITH REMOTE COMMUNICATION APPARATUS FOR AN EXERCISE MACHINE

(76) Inventors: Sarah Grunfeld; Abraham Grunfeld, both of 30 Morris Rd., Spring Valley, NY (US) 10977

( * ) Notice: Subject to any disclaimer, the term of this patent is extended or adjusted under 35 U.S.C. 154(b) by 0 days.

(21) Appl. No.: 09/398,614

(22) Filed: Sep. 17, 1999

(51) Int. Cl.[7] ................................................. A63B 22/00
(52) U.S. Cl. .................................................. 482/54; 482/8
(58) Field of Search ............................... 482/1–9, 51, 54, 482/900–902

(56) References Cited

U.S. PATENT DOCUMENTS 5,076,584 * 12/1991 Openiano ................................ 482/8
5,484,355 * 1/1996 King et al. ............................... 482/4
5,910,070 * 6/1999 Henry et al. ............................. 482/4

* cited by examiner

*Primary Examiner*—Glenn E. Richman
(74) *Attorney, Agent, or Firm*—John D. Gugliotta (57) ABSTRACT

A computer interface with a remote communication apparatus for an exercise machine is disclosed, designed as a stationary exercise machine with provisions for an interactive approach with a predetermined program on a computer-controlled interface and with provisions for interfacing two or more such units to allow a sense of competition between two or more people. The present invention discloses a conventional, stationary exercise machine, a computer with a specialized program or programs, a series of apparatuses for interfacing with the individual exercising as well as the exercise machine itself, and a means for interfacing two or more such machines together.

23 Claims, 6 Drawing Sheets

COMPUTER INTERFACE WITH REMOTE COMMUNICATION APPARATUS FOR AN EXERCISE MACHINE

RELATED APPLICATIONS AND DISCLOSURES

The present invention was first disclosed in the Disclosure Document filed on May 5, 1998. There have been no previously filed, nor any co-pending applications, anywhere in the world.

BACKGROUND OF THE INVENTION

1. Field of the Invention

The present invention relates generally to exercise machines, and, more particularly, to a computer interface with a remote communication apparatus for an exercise machine.

2. Description of the Related Art

The use of stationary exercise machines including treadmills, stationary bikes, and stepping machines has risen in recent times due to the awareness of greater health benefits that result from regular exercise. These machines are found in gyms and health clubs as well as the home. It is not of the ordinary to find individuals that may spend several hours per week on such machines in the quest for a better physique, increased stamina and a higher level of overall general health.

However, many people find such long periods of time boring and repetitious. The surroundings never change, the routing never varies, and the whole workout process just becomes one of tedium until the time limit is obtained, the desired distance is covered, or the number of calories for that session have been burned. The only alternative to this is actual jogging or the riding of a conventional bike outside. However, weather and other factors may prevent individuals from exercising on a regular basis. This is what forced the use of stationary exercise machines in the first place.

While watching television or listening to the radio helps pass the time, while using stationary exercise machines, it does not provide for an interactive exercise session as one would get if actually out jogging or riding a conventional bike. Furthermore, there is no sense of competition when one is using an exercise machine. Competition often pushes individuals to a higher level of achievement and thus a better workout. Accordingly, there is a need for a means by which one can utilize a stationary exercise machine and be afforded an interactive session and a sense of competition while exercising with others.

In the related art, several patents disclose exercise treadmills. These include U.S. Pat. No. 5,209,710, issued in the name of Shimizu et. al. and U.S. Pat. No. 3,826,491, issued in the name of Elder.

Several patents disclose a computerized exercise game machine in the embodiment of an exercise bicycle. These include U.S. Pat. No. 5,362,069, issued in the name of Hall-Tipping, U.S. Pat. No. 5,240,417, issued in the name of Smithson et. al., U.S. Pat. No. 4,976,435, issued in the name of Shatford et. al., U.S. Pat. No. 4,542,891, issued in the name of Melton et. al., U.S. Pat. No. 4,408,613, issued in the name of Relyea.

U.S. Pat. No. 5,667,459, issued in the name of Su, describes a computerized exercise game machine providing feedback to the user.

U.S. Pat. No. 5,205,800, issued in the name of Grant, describes an exercising treadmill with a synchronized video monitor display.

A search of the prior art did not disclose any patents that anticipate directly many features of the instant invention. Consequently, a need has been felt for providing an improved interactive exercise machine that incorporates real time video graphics.

SUMMARY OF THE INVENTION

It is therefore an object of the present invention to provide an improved computer interface with a remote communication apparatus for an exercise machine that provides an interactive exercise session.

Briefly described according to one embodiment of the present invention, a computer interface with a remote communication apparatus for an exercise machine is disclosed, designed as a stationary exercise machine with provisions for an interactive approach with a predetermined program on a computer-controlled interface and with provisions for interfacing two or more such units to allow a sense of competition between two or more people. The present invention discloses a conventional, stationary exercise machine, a computer with specialized program, a series of apparatuses for interfacing with the individual exercising as well as the exercise machine itself, and a means for interfacing two or more such machines together. In the preferred embodiment, the present invention can be sold as a kit for aftermarket installation to existing exercise machines. In an alternate preferred embodiment, the present invention could be built as an integral part of exercise machines at the factory.

A sensor is provided to track speed of the exercise machine. It is envisioned that this sensor would be a wheel-driven device that would match the speed of the exercise machine, be it the belt on a treadmill or a wheel on a stationary bike. An output device is provided to adjust the speed of the exercise machine based upon the program or interface requirements. Two hand controllers are also provided to allow for interfacing to the computer program or interface for such parameters that cannot be derived from the exercise machine motion. These parameters include but are not limited to: left, right, forward, reverse, faster, slower, jump and fire. The jump and fire buttons would be used during various gaming operations performed with the invention.

The user would have the option of playing against a predetermined computer program or against other players. The competition against other players would occur through the use of two or more interconnected machines through the use of a communication path. This path is envisioned to be a serial connection in the case of two or more machines that are in the immediate vicinity to one another, or by the use of a modem connection where the machines are separated by a great distance.

It is an object of the present invention to provide a device that allows for interaction while exercising.

It is another object of the present invention to provide a device that it quickly reprogrammed by the use of computer media for different game or challenge simulations using the same input and output signals for each simulation.

It is another object of the present invention to provide a device that is easily and quickly attached to any conventional exercise machine or can be part of the overall integral design of an exercise machine.

It is another object of the present invention to provide a device that can be quickly and easily activated and deactivated.

It is another object of the present invention to allow for the input of auxiliary signals and provide the associated processing to administer a computer derived health monitor that would track a user's height, weight, blood pressure, heart rate, goals, calories burned, warm up and cool down periods and the like.

It is another object of the present invention to allow for two or more invention equipped exercise machines to connect to one another through the use of the Internet using standard TCP/IP connections. Users may contact one another through the use of email addresses or a common World Wide Web site.

DESCRIPTIVE KEY

| | | | |
|---|---|---|---|
| 10 | computer interface with a remote communication apparatus for an exercise machine | 80 | second gear |
| | | 85 | transducer |
| | | 90 | mounting arm |
| | | 95 | mounting bracket |
| 15 | conventional exercise machine | 100 | attachment straps |
| | | 105 | fastening means |
| 20 | computer | 110 | restraint strap |
| 21 | input port | 115 | servo motor |
| 25 | mounting shelf | 120 | tracking harness |
| 30 | operating panel | 125 | output strap |
| 35 | restraint handles | 130 | motion path arrow |
| 40 | speed adjustment mechanism | 135 | speed control slider |
| 45 | moving element | 140 | first "X" shaped rocker switch |
| 50 | speed detection mechanism | 145 | second "X" shaped rocker switch |
| 55 | first hand controller | | |
| 60 | second hand controller | 150 | modem/network card |
| 65 | interconnecting communication paths | 155 | serial connection cable |
| | | 160 | remote communication link |
| 70 | rubber wheel | 165 | local communication link |
| 75 | first gear | | |

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 1 through 6.

1. Detailed Description of the Figures

Figure 1:
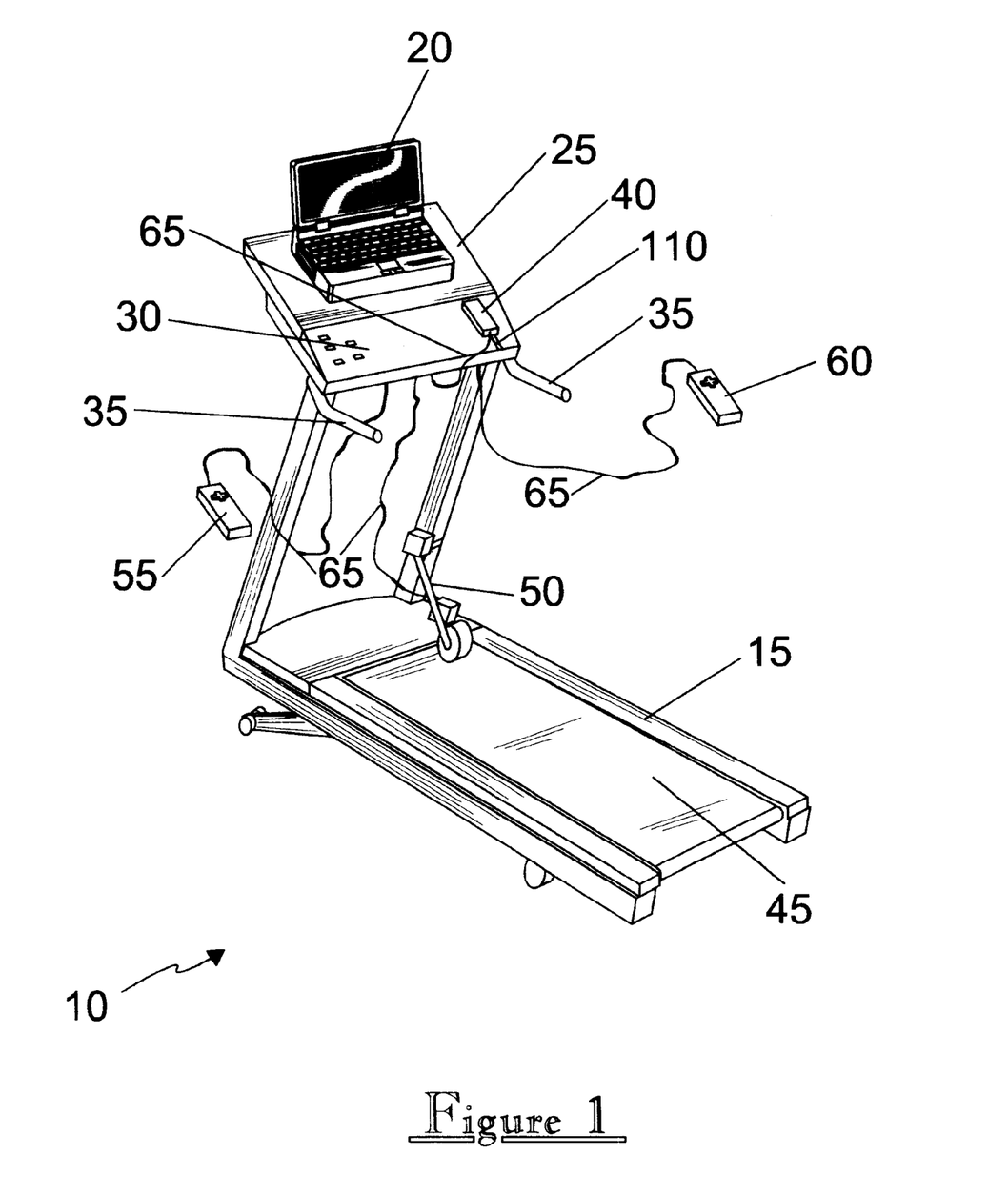
FIG. 1 is a perspective view of the computer interface with a remote communication apparatus for an exercise machine 10 according to a preferred embodiment of the present invention.

Referring now to FIG. 1, a computer interface with a remote communication apparatus for an exercise machine 10 is shown, according to the preferred embodiment of the present invention. A conventional exercise machine 15 is provided upon which all other components are attached. In FIG. 1, the conventional exercise machine 15 is depicted as a treadmill, though it is not intended to be a limiting factor. It is envisioned that a stationary bike or a stair stepping machine would function as the conventional exercise machine 15 in an equally effective manner. A computer 20 is provided at a convenient eye level and is attached to a mounting shelf 25. The computer 20 is depicted as a notebook computer for illustrative purposes only. A conventional computer monitor, or any display means of the appropriate size and weight could be attached to the mounting shelf 25 as well. An additional video port 22 (not shown) on computer 20 could be supplied to allow the connection of display means of any size such as the larger big screen monitors currently popular. An operating panel 30, of the type normally found on a conventional exercise machine 15 is provided in a conventional location above a pair of restraint handles 35 on the preferred embodiment of the present invention. Located on the operating panel 30 is a speed adjustment mechanism 40. The speed adjustment mechanism 40 is a direct part of the computer interface with a remote communication apparatus for an exercise machine 10 and not normally found on a conventional exercise machine 15. The speed adjustment mechanism 40 covers what would normally be the mechanism to control the speed of the conventional exercise machine 15 and is envisioned to be of the linear potentiometer type, although other types could also be accommodated. The speed adjustment mechanism 40 will be described in greater detail herein below. Speed adjustment mechanism 40 is eliminated in the preferred alternate embodiment of the present invention as the speed adjustment means would be built as an integral part of the exercise machine. On the preferred embodiment of the present invention, and located above a moving element 45, such as a walking surface belt on a treadmill, is a speed detection mechanism 50. The speed detection mechanism 50 will be described in greater detail herein below. Speed detection mechanism 50 is eliminated in the preferred alternate embodiment of the present invention as the speed detection means would be built in as an integral part of the exercise machine. Located on the left and right-hand side of the conventional exercise machine 15 is a first hand controller 55 and a second hand controller 60 respectively. Both the first hand controller 55 and the second hand controller 60 are used to control sequences of the program being run by the computer 20 that are not capable of receiving input signals by the speed detection mechanism 50. The first hand controller 55 and the second hand controller 60 will be described in greater detail herein below. The speed adjustment mechanism 40, the speed detection mechanism 50, the first hand controller 55 and the second hand controller 60 are all interconnected to the computer 20 by a series of interconnecting communication paths 65. It is envisioned that a bidirectional data port, such as a parallel port would be utilized for the marshaling of all input and output signals, though other ports or even a proprietary data gathering system would work equally as well.

Figure 2:
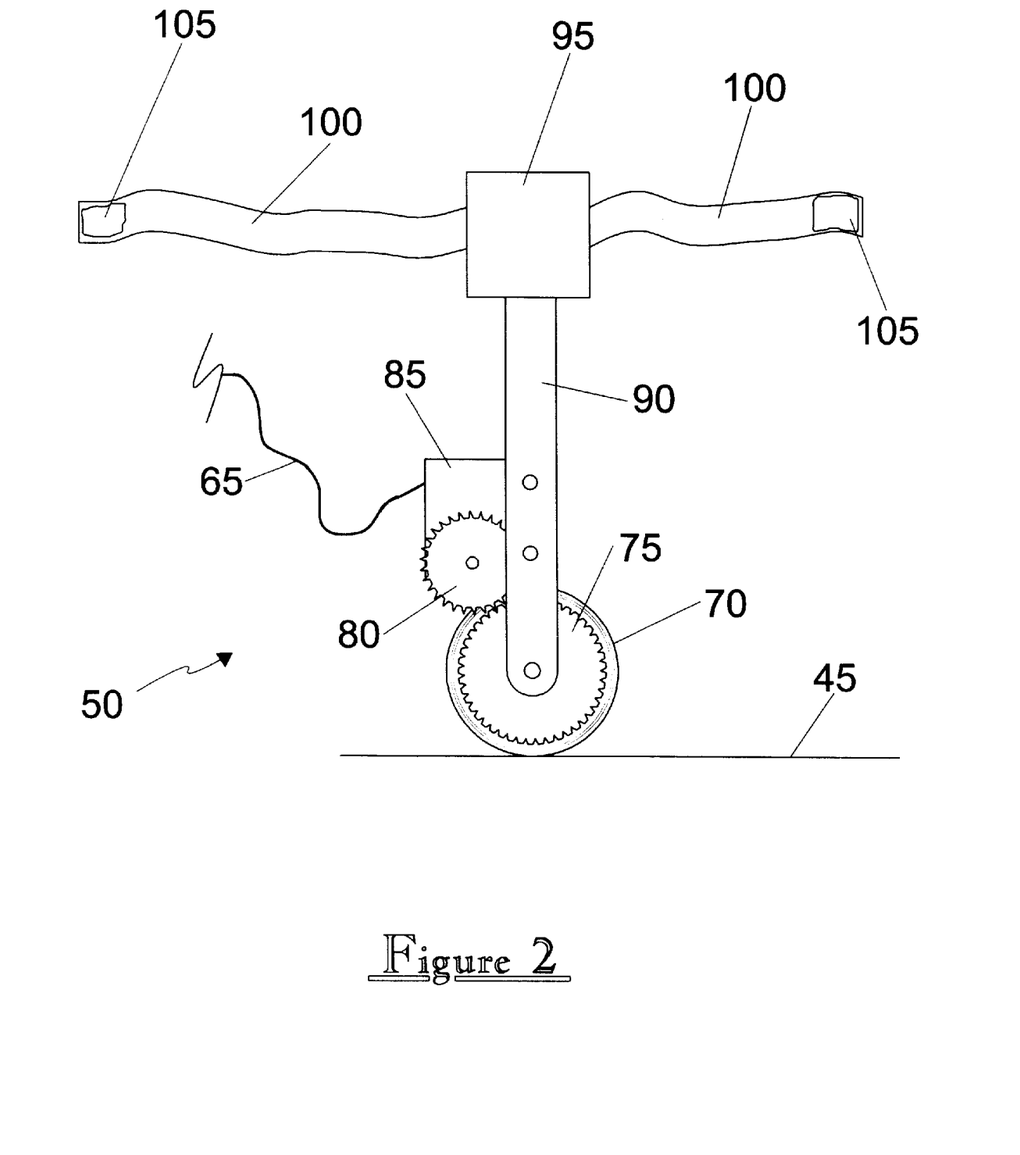
FIG. 2 is a side view of a speed detection mechanism as used on the present invention.

Referring next to FIG. 2, a side view of the speed detection mechanism 50 is disclosed. The speed detection mechanism 50 rides upon the moving element 45 of the computer interface with a remote communication apparatus for an exercise machine 10 (as shown in FIG. 1) and is envisioned to be the walking belt surface of a treadmill or the flywheel on a stationary bike. It is capable of being utilized on any moving surface of any exercise machine. A rubber wheel 70 is held in close physical contact with the moving element 45 by the weight of the speed detection mechanism 50 and thus translates the linear motion of the moving element 45 into a rotational motion. The rubber wheel 70 then imparts this motion onto a first gear 75 by a physical attachment as it turns about its axis. The first gear 75 then turns a second gear 80 located upon a transducer 85. The transducer 85 converts the rotational energy of the transducer 85 into an electrical signal which is transmitted on the interconnecting communication paths 65. All common elements of the speed detection mechanism 50 are directly or indirectly physically attached to a mounting arm 90, which extends from a mounting bracket 95. The mounting bracket 95 is physically connected to the computer interface with a remote communication apparatus for an exercise machine 10 (as shown in FIG. 1) by a set of attachment straps 100 and a set of fastening means 105, such as a hook and loop fastening system. An internal sensor in the transducer 85 detects the level of angle adjustment that has been used on the moving element 45. The main purpose of the speed detection mechanism 50 is to provide input status signals to the computer 20 (as shown in FIG. 1)

Figure 3:
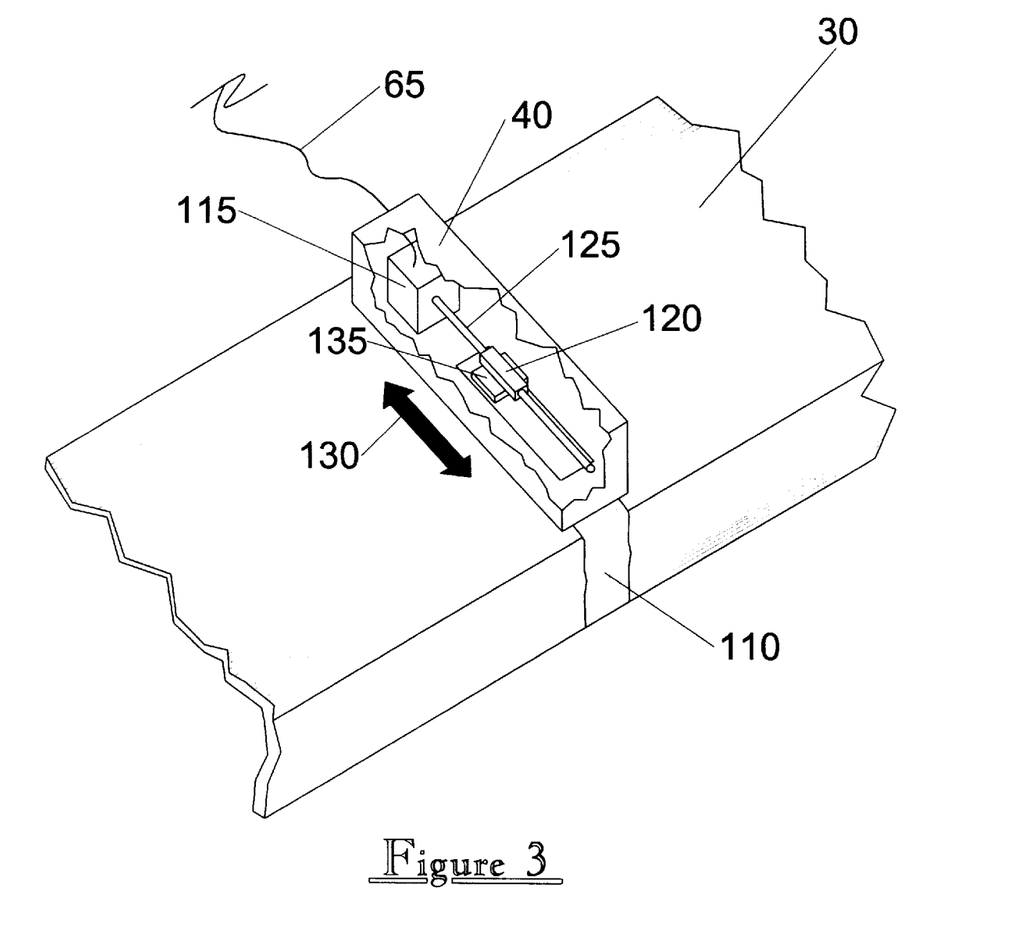
FIG. 3 is a perspective view of a speed adjustment mechanism.

Referring now to FIG. 3, a perspective cutaway view of the speed adjustment mechanism 40 is shown. The speed adjustment mechanism 40 is mounted to the operating panel 30 and held in place by a restraint strap 110. The restraint strap 110 is envisioned to be of the hook and loop fastener variety, though other methods such as a spring or a buckle would work equally as well. Located inside the speed adjustment mechanism 40 is a servo motor 115. The servo motor 115 receives an input signal from the interconnecting communication paths 65 as shown. The servo motor 115 drives a tracking harness 120 along an output strap 125 in a linear motion as depicted by a motion path arrow 130. The tracking harness 120 is held against a speed control slider 135 by friction and close physical contact. As an output signal is received from the computer 20 (as shown in FIG. 1) on the interconnecting communication paths 65, the servo motor 115 generates an appropriate mechanical output on the output strap 125. This locates the tracking harness 120 and thus the speed control slider 135. The position of the speed control slider 135 governs the speed of the moving element 45 on the computer 20 (as shown in FIG. 1) in a manner identical to that if the speed control slider 135 was adjusted manually in a conventional configuration.

Figure 4A:
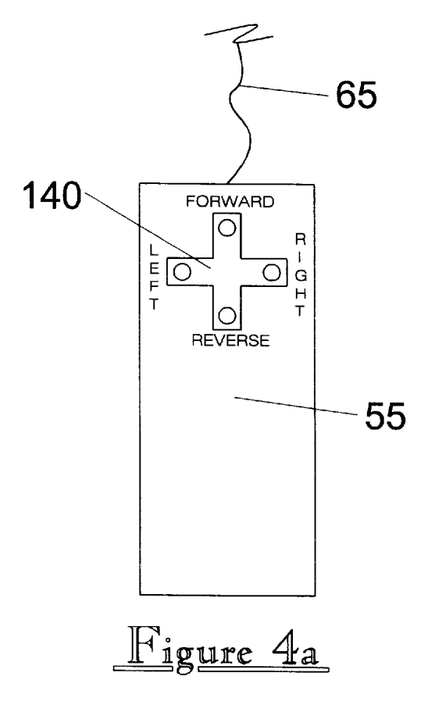
FIG. 4a is a top view of one of two hand controllers.

Referring now to FIG. 4a, a top view of the first hand controller 55 is shown. The first hand controller 55 possesses a first "X" shaped rocker switch 140, similar to that found on video game consoles. The user is capable of activating one of four selections at any one time. The four selections controlled by the first hand controller 55 are: forward, reverse, left and right. The purpose of the first hand controller 55 is to allow the user to control movement, direction and action outside of the action possible on a computer 20 (as shown in FIG. 1). As it is not possible to walk left or right on a treadmill, the user can direct the program to take such action through the use of the first hand controller 55. The output signals of the first hand controller 55 are directed as an input signal to the computer 20, (as shown in FIG. 1) thorough the use of the interconnecting communication paths 65. As the interconnecting communication paths 65 is depicted as a cable for illustrative purposes, it should be understood that any communication path such as infrared, ultrasonic, microwave, radio frequency (RF) and the like along with any type of cabled connection using any type of cable could also be utilized.

Figure 4B:
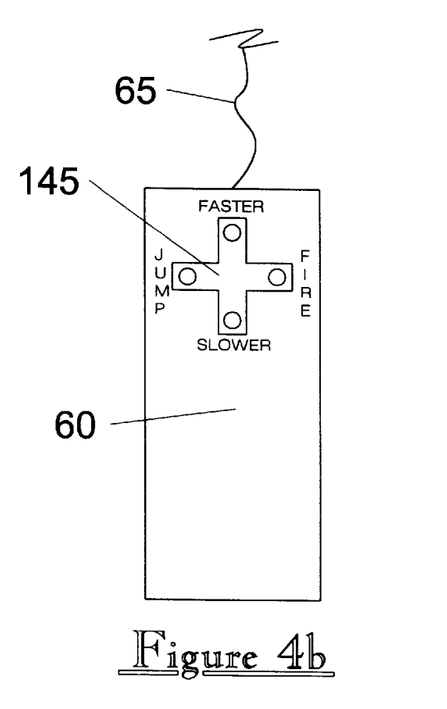
FIG. 4b is a top view of the other hand controller.

Referring now to FIG. 4b, a top view of the second hand controller 60 is shown. The second hand controller 60 is provided with an interconnecting communication path 65 in a manner equal to that of the interconnecting communication paths 65 supplied with the first hand controller 55 (as shown in FIG. 4a). The second hand controller 60 is provided with a second "X" shaped rocker switch 145 that provides for the following four actions: faster, slower, jump, and fire. It should be noted that the jump and fire buttons would be used while playing various roll playing games against the computer 20 (as shown in FIG. 1) or other players. The games would be envisioned as basketball, chases, cops and robbers, and the like. The selections as provided by the first "X" shaped rocker switch 140 and the second "X" shaped rocker switch 145 would be capable of being reassigned by the computer 20, and would be dependent on the game or event being played.

Figure 5:
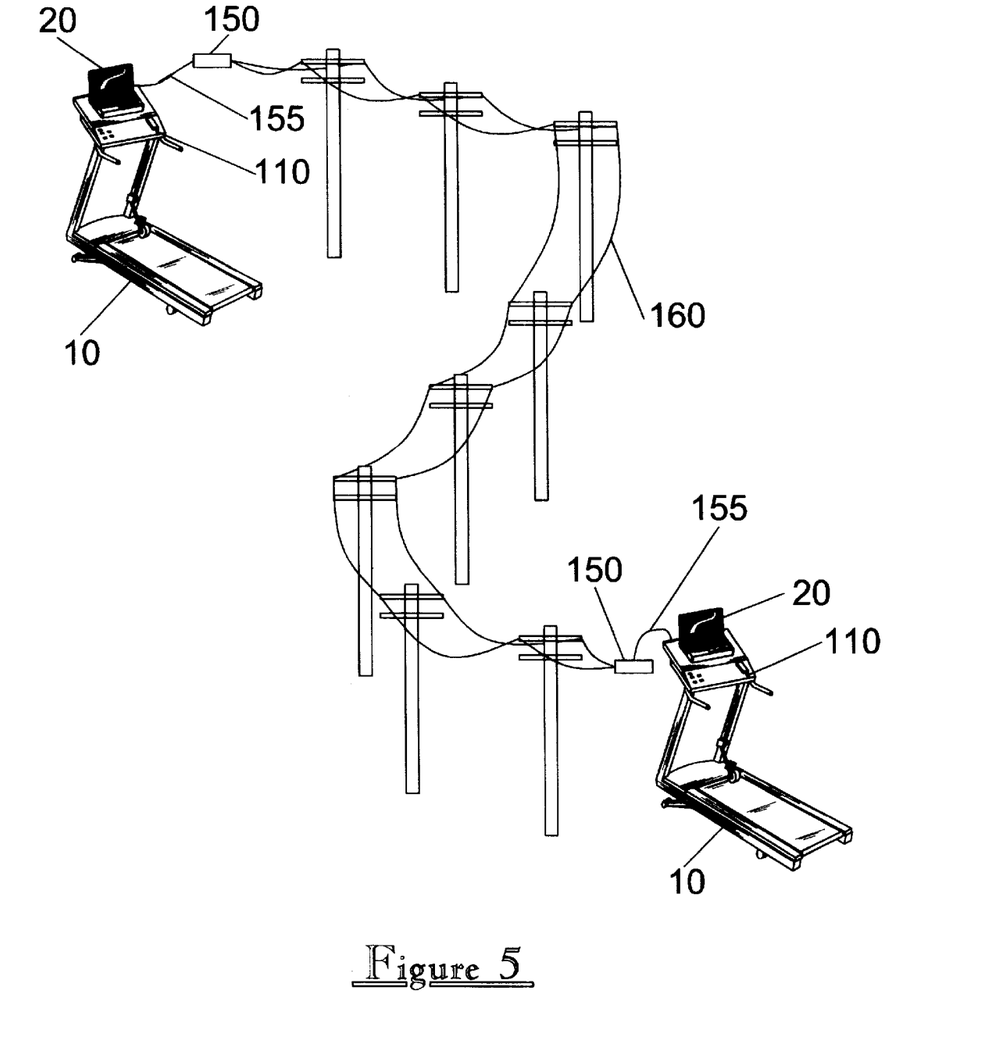
FIG. 5 is an interconnection diagram of the computer interface with a remote communication apparatus for an exercise machine 10 when used with a remote interconnection communication path.

Referring next to FIG. 5, an interconnection diagram of the computer interface with a remote communication apparatus for an exercise machine 10 when used with a remote interconnection communication path is disclosed. A modem/network card 150 is connected to the computer 20 of each computer interface with a remote communication apparatus for an exercise machine 10 by use of serial connection cable 155. The modem/network card 150 is depicted as a separate component for illustrative purposes but could also be an integral part of the computer 20. The modem/network card 150 is used to establish a remote communication link 160 between one or more computer interface with a remote communication apparatus for an exercise machine 10 for the purpose of establishing competition or the engaging in game playing. The remote communication link 160 is envisioned to be a direct dial up connection. However, those familiar in the art, realize that other means such as a local area network, a wide area network, packet system, a TCP/IP system, using the Internet or other similar network could also be used with equal success. It is envisioned that if the computer interface with a remote communication apparatus for an exercise machine 10 is used with the Internet, a World Wide Web site with links to other players wishing to engage in a game could meet for the purposes of game playing. Various players could contact one another through the use of e-mail addresses or another proprietary format for the purposes of competition or gaming.

Figure 6:
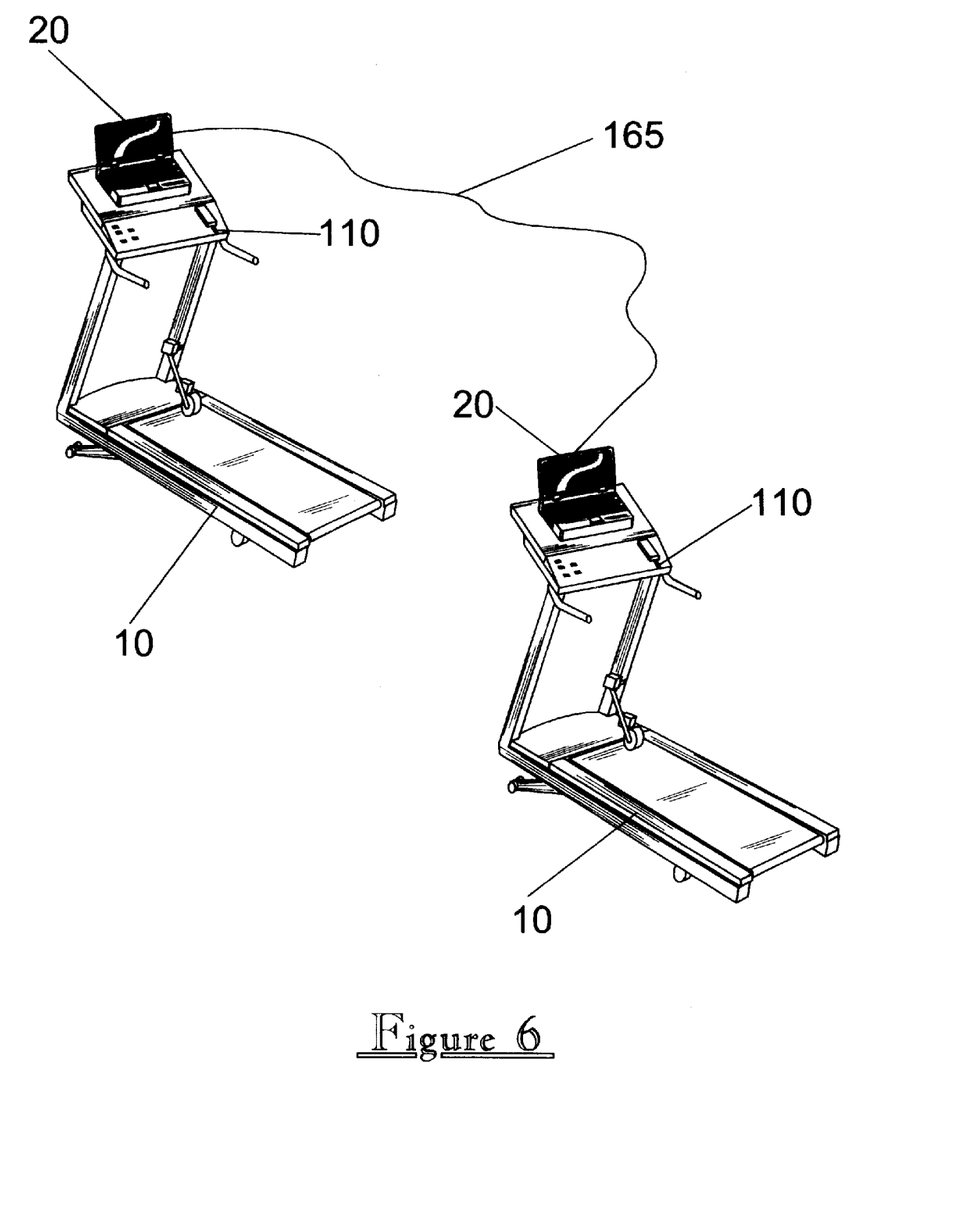
FIG. 6 is an interconnection diagram of the computer interface with a remote communication apparatus for an exercise machine 10 when used with a local interconnection communication path.

Referring finally to FIG. 6, an interconnection diagram of the computer interface with a remote communication apparatus for an exercise machine 10 when used with a local interconnection communication path is disclosed. A set of one or more computer interface with a remote communication apparatus for an exercise machine 10 is connected by a local communication link 165 through the use of the computer 20. This setup would be used when the computer interface with a remote communication apparatus for an exercise machine 10 are in close physical proximity to one another such as in a health club, a workout center, a gym or a home.

The software used with the computer 20 to interface with the computer interface with a remote communication apparatus for an exercise machine 10 forms an integral part of this disclosure. The software would be universal in nature that would allow for new games, situations and revisions to be released and played upon the computer interface with a remote communication apparatus for an exercise machine 10 in much the same manner as new computer programs and video games are released today that play upon existing computers and video game consoles. Only a few of the many possible situations and variations will be listed here for informational purposes. All of the information that is displayed on conventional high-end exercise machines such as distance covered, calories burned, speed, time and the like would also be displayed upon the computer 20. In addition, the storage capabilities of a computer allow for the tracking of performance and improvements thereto over time. An approved exercise regimen can be custom designed and tracked using the computer 20. It is also envisioned that a software-based health advisor would perform this custom designed regimen using such inputted factors as weight, height, age, medical history and so forth. Such a health advisor would also suggest an appropriate warm up and cool down period for the type of exercising to be performed. The health advisor could also track goals, calories burned, time limits and distance covered as aforementioned described. An additional modification to the health advisor approach would be a set of sensors that tracked the user's heart rate and blood pressure as well. The health advisor would be used in conjunction with any game or simulation that would be run on the computer interface with a remote communication apparatus for an exercise machine 10. Some simulations would be running or bicycling in any part of the world through the use of prerecorded sessions. It should be remembered that it is an interactive approach where the user can control the route to be taken through the use of the first hand controller 55 and the second hand controller 60. Games where the computer would generate obstacles to be avoided will also be developed. Finally, any game or simulation could be played by more than one player by the interconnection described earlier in FIG. 5 and FIG. 6. These games would be supplied on a suitable computer storage medium such as CD's, DVD's, cartridges type "memory" packs through an input port 21 to said computer, or direct download from the Internet via said modem or via said network card from a network or other source connected to the Internet.

It is envisioned that other styles and configurations of the present invention can be easily incorporated into the teachings of the present invention, and only one particular configuration shall be shown and described for purposes of clarity and disclosure and not by way of limitation of scope.

2. Operation of the Preferred Embodiment

To use the preferred embodiment of the present invention, the user must first install the computer 20 and associated components onto the conventional exercise machine 15. Mounting shelf 25 would be mounted to the exercise machine 15. Next, computer 20 would be mounted to the mounting shelf 25. Next, the speed adjustment mechanism 40 would be installed on the speed control slider 135 as indicated. The speed detection mechanism 50 would also be mounted using the mounting bracket 95. Finally all interconnecting communication paths 65 would be connected and verified operational. At this point the computer interface with a remote communication apparatus for an exercise machine 10 is ready for use. It is also envisioned in those cases where the computer 20 and the conventional exercise machine 15 are an integral unit, no user assembly would be required.

The user would activate the desired program on the computer 20 in the same manner that conventional computer games are started. After the necessary starting information is gathered, the user would begin using the computer interface with a remote communication apparatus for an exercise machine 10 in a manner normally consistent with a conventional exercise machine 15. The action would be directed by the use of the first hand controller 55 and the second hand controller 60 and necessary output corrections would be made by the computer 20 using the speed adjustment mechanism 40. The user would complete his or her exercise regimen in an interactive environment in a much more interesting atmosphere than normally associated with the use of conventional exercise machines.

If the user of the computer interface with a remote communication apparatus for an exercise machine 10 wished to interact with another, an appropriate communication link would be established in general conformance with FIG. 5 of FIG. 6, depending on the location of the other user. The remainder of the exercise regimen would continue as described above. It is also envisioned that real time chat features as well as video transmission of the other participants would be possible as well using existing computer peripherals.

The foregoing description is included to illustrate the operation of the preferred embodiment and is not meant to limit the scope of the invention. The scope of the invention is to be limited only by the following claims.

What is claimed is:

1. A computer interface with a remote communication apparatus for an exercise machine, designed for use with a conventional exercise machine, said computer interface with a remote communication apparatus for an exercise machine comprising:

a computer, said computer being capable of running programs, and said computer having a computer monitor, and said computer and computer monitor located at a convenient eye level at the anterior of the exercise machine;

a mounting shelf, said mounting shelf releasably attached to the side rails of said exercise machine via a clamp and used to support said computer;

a speed adjustment mechanism, said speed adjustment mechanism located on a operating panel located on the exercise machine and electronically connecting the computer with the exercise machine;

a speed detection apparatus, said speed detection apparatus designed to monitor the speed generated by the exercise machine;

a first hand controller, said first hand controller located on the left-hand side of the conventional exercise machine, and designed to control sequences of the program run by the computer that are not capable of receiving input signals by the speed detection mechanism;

a second hand controller, said second hand controller located on the right-hand side of the conventional exercise machine, and designed to control sequences of the program run by the computer that are not capable of receiving input signals by the speed detection mechanism;

electronic interconnecting communication paths, said electronic interconnecting communication paths electronically connecting said speed adjustment mechanism, speed detection mechanism, first hand controller and the second hand controller to the computer.

2. The computer interface with a remote communication apparatus for an exercise machine described in claim 1, wherein said speed detection mechanism provides input status signals to the computer, and further comprises:

a rubber wheel, said rubber wheel held in close physical contact with said moving element by the weight of the speed detection mechanism and thus translates the linear motion of the moving element into a rotational motion;

a first gear, said first gear receiving the rotational motion of the rubber wheel by physical attachment as said rubber wheel turns about its axis;

a second gear, said second gear receiving the rotational motion of the first gear by physical contact as the first gear turns about its axis;

a transducer, said transducer connected to said second gear and said transducer converting the rotational energy of the second gear into an electrical signal which is transmitted on said interconnecting communication paths to said computer;

a mounting bracket, said mounting bracket releasably attached to said exercise machine via a set of attachment straps and a set of fastening means;

a mounting arm, said mounting arm attached to said mounting bracket, and used to secure and support the other components of the speed detection mechanism; and an internal sensor, said internal sensor located in the transducer and designed to detect the level of angle adjustment that has been used on the moving element and send this information to the computer.

3. The computer interface with a remote communication apparatus for an exercise machine described in claim 1, wherein said speed adjustment mechanism further comprises:

a servo motor, said servo motor receiving an input signal from the interconnecting communication paths;

a tracking harness, said tracking harness driven by said servo motor;

a speed control slider, said speed control slider held against said tracking harness by friction and close physical contact.

4. The computer interface with a remote communication apparatus for an exercise machine of claim 3, wherein as an output signal is received from the computer on the interconnecting communication paths, the servo motor generates an appropriate mechanical output on the output strap, which locates the tracking harness and thus the speed control slider.

5. The computer interface with a remote communication apparatus for an exercise machine of claim 1, wherein the position of the speed control slider governs the speed of the moving element on the computer in a manner identical to that if the speed control slider was adjusted manually in a conventional exercise machine configuration.

6. The computer interface with a remote communication apparatus for an exercise machine described in claim 1, wherein first hand controller possesses a first "X" shaped rocker switch, similar to that found on video game consoles, thus enabling the user to activate one of four selections at any one time.

7. The computer interface with a remote communication apparatus for an exercise machine described in claim 1, wherein said second hand controller possesses a second "X" shaped rocker switch, similar to that found on video game consoles, thus enabling the user to activate one of four selections at any one time.

8. The computer interface with a remote communication apparatus for an exercise machine described in claim 1, wherein said interconnecting communication paths are selected from the group comprising cable, infrared, ultrasonic, microwave, and radio frequency (RF).

9. The computer interface with a remote communication apparatus for an exercise machine described in claim 1, further comprised of a remote interconnection communication path connected to said computer to establish a remote communication link between one or more computer interface with a remote communication apparatus for an exercise machine for the purpose of establishing competition or the engaging in game playing, said remote communication apparatus selected from the group comprising modem and network card connected via a serial cable to said interconnection communication path selected from the group comprising dial up connection, local area network, wide area network, packet system, and TCP/IP system using the Internet.

10. The computer interface with a remote communication apparatus for an exercise machine described in claim 1, further comprised of a local interconnection communication path connected to said computer to establish a local communication link between one or more computer interface with a remote communication apparatus for an exercise machine for the purpose of establishing competition or the engaging in game playing, said local interconnection communication path consists of a serial cable.

11. The computer interface with a remote communication apparatus for an exercise machine described in claim 1, wherein said software programs consists of software universal in nature to be played upon said computer for different games or challenge situations subject to revision and supplied on a suitable computer storage medium selected from the group comprising CD's, DVD, cartridge type "memory" packs through an input port to said computer, or direct download from the Internet via said modem or via said network card from a network or other source connected to the Internet.

12. The computer interface with a remote communication apparatus for an exercise machine described in claim 11, further comprised of a set of sensors to track the user's heart rate and blood pressure as part of a health advisor software approach to be used in conjunction with said software for said games or simulations that would be run on said computer interface with a remote communication apparatus.

13. An exercise machine with a built in computer interface with a remote communication apparatus, said computer interface with a remote communication apparatus for said exercise machine comprising:

a computer, said computer being capable of running programs, and said computer having a computer monitor, and said computer and computer monitor located at a convenient eye level at the anterior of the exercise machine;

a speed adjustment mechanism, said speed adjustment mechanism designed to adjust the speed of the exercise machine electronically connecting the computer with the exercise machine;

a speed detection apparatus, said speed detection apparatus designed to monitor the speed generated by the exercise machine;

a first hand controller, said first hand controller located on the left-hand side of the conventional exercise machine, and designed to control sequences of the program run by the computer that are not capable of receiving input signals by the speed detection mechanism;

a second hand controller, said second hand controller located on the right-hand side of the conventional exercise machine, and designed to control sequences of the program run by the computer that are not capable of receiving input signals by the speed detection mechanism;

electronic interconnecting communication paths, said electronic interconnecting communication paths electronically connecting said speed adjustment mechanism, speed detection mechanism, first hand controller and the second hand controller to the computer.

14. The exercise machine with a built in computer interface with a remote communication apparatus described in claim 13, wherein said speed detection mechanism provides input status signals to the computer.

15. The exercise machine with a built in computer interface with a remote communication apparatus of claim 14, wherein as an output signal is received from the computer on the interconnecting communication paths, the speed adjustment mechanism adjusts the speed of the moving element on the exercise machine.

16. The exercise machine with a built in computer interface with a remote communication apparatus of claim 15, wherein the position of the speed control slider governs the speed of the moving element on the computer in a manner identical to that if the speed control slider was adjusted manually in a conventional exercise machine configuration.

17. The exercise machine with a built in computer interface with a remote communication apparatus of claim 16, wherein first hand controller possesses a first "X" shaped rocker switch, similar to that found on video game consoles, thus enabling the user to activate one of four selections at any one time.

18. The exercise machine with a built in computer interface with a remote communication apparatus of claim 17, wherein said second hand controller possesses a second "X" shaped rocker switch, similar to that found on video game consoles, thus enabling the user to activate one of four selections at any one time.

19. The exercise machine with a built in computer interface with a remote communication apparatus of claim 18, wherein said interconnecting communication paths are selected from the group comprising cable, infrared, ultrasonic, microwave, and radio frequency (RF).

20. The exercise machine with a built in computer interface with a remote communication apparatus of claim 19, further comprised of a remote interconnection communication path connected to said computer to establish a remote communication link between one or more computer interface with a remote communication apparatus for an exercise machine for the purpose of establishing competition or the engaging in game playing, said remote communication apparatus selected from the group comprising modem and network card and connected via a serial cable to said interconnection communication path selected from the group comprising dial up connection, local area network, wide area network, packet system, and TCP/IP system using the Internet.

21. The exercise machine with a built in computer interface with a remote communication apparatus of claim 20, further comprised of a local interconnection communication path connected to said computer to establish a local communication link between one or more computer interface with a remote communication apparatus for an exercise machine for the purpose of establishing competition or the engaging in game playing, said local interconnection communication path consisting of a cable.

22. The exercise machine with a built in computer interface with a remote communication apparatus of claim 21, wherein said programs consists of software universal in nature to be played upon said computer for different games or challenge situations subject to revision and supplied on a suitable computer storage medium selected from the group comprising CD's, DVD's, cartridge type "memory" packs through an input port to said computer, or direct download from the Internet via said modem or via said network card from a network or other source connected to the Internet.

23. The exercise machine with a built in computer interface with a remote communication apparatus of claim 22, further comprised of a set of sensors to track the user's heart rate and blood pressure as part of a health advisor software approach to be used in conjunction with said software for said games or simulations that would be run on said computer interface with a remote communication apparatus.

\* \* \* \* \*